(12) United States Patent
Blair et al.

(10) Patent No.: US 6,632,462 B2
(45) Date of Patent: Oct. 14, 2003

(54) BLACK TEA MANUFACTURE

(75) Inventors: Ruth Louisa Blair, Bedford (GB); Robert Ong'Ondi Mayaka, Kericho (KE); Andrew David Parry, Bedford (GB); Peter Joseph Stabler, Bedford (GB)

(73) Assignee: Lipton, division of Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 09/841,823

(22) Filed: Apr. 25, 2001

(65) Prior Publication Data

US 2001/0048956 A1 Dec. 6, 2001

(30) Foreign Application Priority Data

Apr. 27, 2000 (GB) .............................................. 0010315

(51) Int. Cl.[7] .............................. A23F 3/00; A23F 3/08; A23F 3/12
(52) U.S. Cl. ......................................... 426/49; 426/597
(58) Field of Search .................................... 426/597, 49

(56) References Cited

U.S. PATENT DOCUMENTS

| 3,438,785 A | | 4/1969 | Zameitat et al. |
| 3,812,266 A | | 5/1974 | Sanderson et al. |
| 4,051,264 A | | 9/1977 | Sanderson et al. |
| 5,250,317 A | * | 10/1993 | Liu et al. |
| 5,863,581 A | * | 1/1999 | Barrett et al. |
| 6,036,991 A | | 3/2000 | Humphrey et al. |
| 6,299,926 B1 | * | 10/2001 | Balakrishnan et al. |

FOREIGN PATENT DOCUMENTS

| WO | WO 99/40799 | 8/1999 |
| WO | WO 00/10401 | 3/2000 |
| WO | WO 00/47057 | 8/2000 |
| WO | WO 01/11979 A1 | 2/2001 |

OTHER PUBLICATIONS

UK Patent Search (GB 0010315.0).
WPI Abstract and Accession No. 1987–068992 & JP 620022549 (Okamoto) Jan. 30, 1987.
WPI Abstract and Accession No. 1978–23159A & SU 562260 (Dzneladze) Aug. 1, 1977.
"Tea: Cultivation to Consumption" edited by K.C. Wilson and M.N. Clifford, Chapman & Hall 1992.

* cited by examiner

Primary Examiner—Anthony J. Weier (57) ABSTRACT

A process for manufacturing black leaf tea that looks and feels like orthodox processed tea but has the liquor characteristics of a fuller fermented CTC processed tea. The process involves withering a first supply of freshly plucked tea leaves, macerating the withered leaves, allowing the macerated withered leaves to ferment to produce macerated dhool, withering a second supply of freshly plucked tea leaves, mixing the macerated dhool obtained from the first supply of leaves with the withered leaves obtained from the second supply of leaves, rolling the mixture, allowing the rolled mixture to ferment, and drying the fermented mixture to yield black leaf tea.

8 Claims, 4 Drawing Sheets

BLACK TEA MANUFACTURE

The present invention relates to tea processing, or more specifically, a process for manufacturing a black leaf tea that resembles orthodox processed tea but possesses infusion characteristics more akin to CTC processed tea.

BACKGROUND AND PRIOR ART

Leaf tea may be prepared as green leaf tea or black leaf tea. Generally, to prepare black leaf tea fresh green leaves of the plant *Camellia sinensis* are withered (subjected to mild drying), comminuted, fermented (in which process enzymes in the tea leaf use atmospheric oxygen to oxidise various substrates to produce brown-coloured products) and then fired (to dry the tea leaves). Green leaf tea is not exposed to the fermentation process. Partial fermentation may be used to produce intermediate-type teas known as "oolong" tea.

Conventional wisdom dictates that in black tea manufacture tea must be macerated in some way to liberate the fermentative enzymes and their substrates within the leaves. One can macerate tea in many ways but broadly speaking there are two main mechanised methods for doing this.

The first, called "orthodox manufacture", involves rolling pre-weighed batches of withered tea leaves prior to fermenting, firing and drying steps. So called "orthodox tea" is typically characterised by leaf particles that are aesthetically pleasing to many (resemble dried leaves rather than "granules" of CTC tea—see below) but produce lighter liquors due to less extensive fermentation.

The second method is the most popular of a number of non-orthodox, continuous methods that involves using a machine resembling a mangle that cuts, tears and curls tea leaves. The original machine was invented by W. McKercher in 1930 and is commonly referred to as a CTC (cut-tear-curl) machine. The finely cut product is known generically as "CTC tea" and is characterised by a fast infusion rate and strong colour. This method tends to produce tea that is more consistent and uniform in quality and than the orthodox method.

Both orthodox and CTC machines are often used in conjunction with a rotorvane machine, which is a type of extruder used to pre-condition (squeeze/shred) leaves prior to maceration. The rotorvane was invented as a form of continuous orthodox roller, but is rarely used as such today. Liquors generated from rotorvane teas are similar to orthodox in terms of liquor properties and infusion rates. These methods and their history and role in tea manufacture are described in "Tea: Cultivation to Consumption" edited by K. C. Willson and M. N. Clifford, Chapman & Hall, 1992.

Generally speaking consumer preference for either orthodox or CTC tea is a matter of national or regional culture. In many countries the visual appearance and texture of leaf tea are important indicators of quality, larger leaf particles being associated with higher quality. In Western markets tea is increasingly purchased in filter paper bags and the colour of the infused product tends to be more important.

Some consumers however want the best of both worlds; i.e. a leaf tea that looks and feels like orthodox processed tea but has the liquor characteristics of a fuller fermented CTC processed tea. Unfortunately there is no commercially available tea manufacturing equipment that can deliver such a leaf tea.

In response to those needs, the applicant has developed methods for manufacturing black leaf teas that resemble orthodox processed tea but infuse like CTC processed tea.

Our international patent application WO 99/40799 discloses one method for manufacturing fast infusing whole or large leaf teas that involves subjecting whole tea leaves to a heat shock at a temperature and for a duration that is sufficient to initiate fermentation, and enabling the tea to ferment for a time and at a temperature that is sufficient to achieve desired liquor properties.

Our international patent application WO 00/10401 discloses another method for manufacturing fast infusing whole or large leaf teas. In that method whole leaf tea is impregnated tea leaves with liquid carbon dioxide within a pressure vessel, depressurising the vessel at a rate that is sufficient to freeze the liquid carbon dioxide, applying sufficient heat to cause the frozen carbon dioxide to sublime and consequently initiate fermentation within the leaves, allowing the tea to ferment for a time that is sufficient to achieve desired liquor properties, and drying the fermented product to yield the whole leaf tea.

The present inventors have developed a third method for manufacturing black leaf teas that resemble orthodox processed tea but infuse like CTC processed tea. This method provides at least a useful alternative to those methods, and has the advantage of potentially utilising existing tea manufacturing equipment (but in a novel fashion; although novel equipment can also be utilised to roll and/or mix the two dhool streams).

STATEMENT OF THE INVENTION

In broad terms the present invention relates to a process for manufacturing black tea comprising the steps of: withering a first supply of freshly plucked tea leaves, macerating the withered leaves, allowing the macerated withered leaves to ferment to produce macerated dhool; withering a second supply of freshly plucked tea leaves; mixing the macerated dhool obtained from said first supply of leaves with the withered leaves obtained from said second supply of leaves, rolling the mixture, allowing the rolled mixture to ferment; and drying the fermented mixture to yield black leaf tea.

Black leaf tea made in this way resembles orthodox processed leaf tea but infuses in freshly boiled water at a rate in excess of that of the equivalent mass of the same size grade tea that has undergone orthodox processing. Indeed the tea preferably infuses at a rate that is comparable to that of the equivalent mass of the same tea that has undergone CTC processing.

The first supply of freshly plucked tea leaves is preferably macerated using a CTC machine. It is especially preferable to pass the leaves through a rotorvane machine and then a CTC machine.

The macerated dhool preferably comprises between 10 and 50% of the mixture on a dry weight basis, especially between 15 and 40%, more especially about 35%.

There is a custom (particularly practised in South India) of adding tea dust back in to the tea manufacturing process (usually the CTC process). Such teas are termed "reconditioned", and the objective is to "upgrade" poor quality dust through its incorporation in to new grades. These teas are judged to be poor quality by tea tasters. The present inventors have shown that even when high quality dust is used in the process of the present invention (in place of dhool) a lower quality (less coloured liquor) product results compared to when dhool is used.

The mixture of the macerated dhool obtained from said first supply of leaves and the withered leaves obtained from said second supply of leaves is preferably rolled using a rotorvane machine.

"Tea" for the purposes of the present invention means leaf material from *Camellia sinensis* or *Camellia assamica*. It also includes rooibos tea obtained from *Aspalathus linearis* however that is a poor source of endogenous fermenting enzymes. "Tea" is also intended to include the product of blending two or more of any of these teas.

"Leaf tea" means tea that contains one or more tea origins in an uninfused form.

"Black leaf tea" means substantially fermented leaf tea.

For the avoidance of doubt the word 'comprises' is intended to mean including but not necessarily "consisting of" or "composed of". In other words the listed steps or options need not be exhaustive.

DETAILED DESCRIPTION OF THE INVENTION

The process of the present invention combines steps normally associated with CTC manufacture with those normally associated with orthodox manufacture in a way that allows the consumer to enjoy the best of both worlds.

Figure 1:
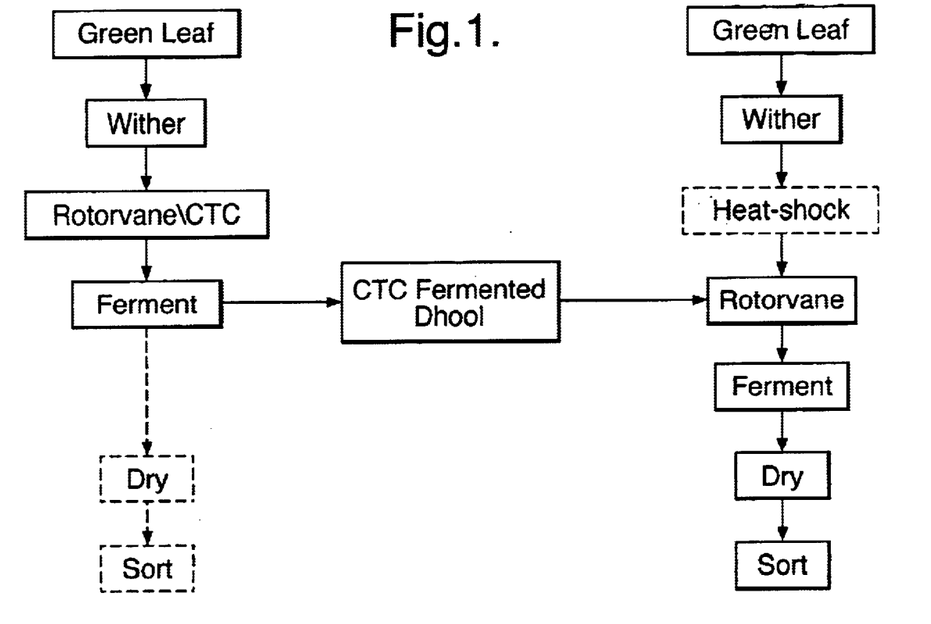
FIG. 1 shows a flow chart of the process.

The process is represented as a flow chart in FIG. 1.

In the process a first supply of freshly plucked tea leaves (so called green leaf) is withered in a conventional manner. This involves storing the tea leaves for a period of time, usually perhaps up to 24 hours, during which time they undergo various biochemical and physical changes and typically lose moisture (from about 74 to 85% in freshly plucked leaves, depending on the climate and the amount of surface moisture, to between 68% or less up to 74 to 78%).

The withered leaves are then macerated by some suitable means. This involves cutting and tearing the leaves in order to liberate the fermentable substrates and fermenting enzymes such as polyphenol oxidase (PPO) that are contained in the plant cells and tissue. CTC (cut-tear-curl) machines are typically used for this purpose and are the machines of choice for the present inventors too. It is preferable to pass the leaves thorough a rotorvane machine first as the rolling and coarse cutting that is gives conditions the leaves for a more fine cutting and tearing by the CTC machine.

The macerated leaves are then left to ferment. The term "fermentation" is commonly used in the context of brewing alcohol to describe the action of exogenous enzymes. However in the tea world it is used to refer to the oxidative process that tea undergoes when certain endogenous enzymes and substrates are brought together following the disruption of the cell walls and tissues. During this process colourless catechins in the leaves are converted to a complex mixture of yellow and orange to dark-brown substances and a large number of aromatic volatile compounds are also produced.

The macerated leaves should preferably be allowed to ferment for at least 30 minutes, more preferably at least 90 minutes, and ideally for 100 to 160 minutes. Leaving the leaves to ferment for longer than three hours can detrimentally effect the quality of the final product. It can also have cost implications. These times are dependent on the ambient temperatures, but are comparable to conventional times for fermentation of CTC tea.

Fermentation is preferably conducted at ambient temperature, i.e. about 25° C., although 18° C. or even 15° C. can be suitable. If desired, fermentation can be accelerated at slightly higher temperatures such as 30 to 40° C. The use of an oxygen-enriched atmosphere in a fermentation vessel is also beneficial.

The mass of fermented leaf macerate is known as known as dhool. It typically has a high moisture content, for example about 62 to 74%.

If desired, the dhool can be treated with tannase (flavanol gallate esterase) to generate degallated catechins and gallic acid (which subsequently leads to the generation of high levels of theaflavins and non-gallated thearubigins during fermentation) or treated with tannase followed by hydrogen peroxide in a quantity that is sufficient for the endogenous peroxidases to oxidise gallic acid liberated by the tannase treatment. These treatments generate coloured species and enhance flavour. They are described in detail in our international patent application PCT/GB00/00359, the disclosure of which is incorporated herein by reference.

Alongside this, a second supply of freshly plucked tea leaves (so called green leaf) is withered in a conventional manner, preferably to a moisture level of 62 to 68% (that is a "harder" wither than the leaf in the first stream).

If desired, one can initiate fermentation in the withered leaves by subjecting the leaves to a heat shock at a temperature and for a duration that is sufficient to initiate fermentation as described in our international patent application WO 99/40799. Alternatively, one could impregnate the withered tea leaves with liquid carbon dioxide within a pressure vessel, depressurise the vessel at a rate that is sufficient to freeze the liquid carbon dioxide, apply sufficient heat to cause the frozen carbon dioxide to sublime and consequently initiate fermentation within the leaves, allow the tea to ferment for a time that is sufficient to achieve desired liquor properties, and dry the fermented product to yield the whole leaf tea. Such a method is described in our international patent application WO 00/10401. A further alternative method of disrupting the leaves and initiating fermentation of rolled leaves is to subject the leaves to cycles of freezing and thawing.

The withered leaves obtained from the second supply of tea leaves are mixed with the fermented dhool that has been obtained from the first supply of tea leaves. The macerated dhool preferably comprises between 10 and 50% of the mixture on a dry weight basis, especially between 15 and 40%, more especially about 35%.

One could mix the macerated fermented dhool obtained from the first supply of tea leaves with withered tea leaves obtained from the second supply of tea leaves that have already been rolled, however the differently processed leaves are less likely to adhere to each other and could separate during storage and provide inconsistent results when blended with other teas.

The mixture is then rolled (as opposed to macerated) using machinery that one might otherwise use to manufacture orthodox tea. A rotorvane machine is ideally suited to this purpose. It is also envisaged that alternative equipment (such as an extruder) could perform this task, performing the key actions of mixing and squeezing/rolling the dhool and withered leaves.

The rolled mixture is left to ferment. The present inventors have found that the mixture should be left to ferment for at least more than one hour, preferably more than two hours but again not more than 3 hours. A fermentation time of about 140 minutes is especially preferred.

Once again, the fermentation is preferably conducted at ambient temperature, i.e. about 25° C., although 18° C. or even 15° C. can be suitable. If desired, fermentation can be accelerated at slightly higher temperatures such as 30 to 40° C. The use of an oxygen-enriched atmosphere in a fermentation vessel is also beneficial.

The inventors, and expert tea tasters, were very surprised at the quality of the product produced by the process of the invention. One might have expected that as a significant proportion of this dhool mixture has been fermented (the first or CTC portion) once before mixing, "overfermented" flavours would be generated during the fermentation of the mixture and therefore a dull liquor would result (as is known from long fermentations of conventional tea). However no such notes or flaws were observed in the product. An understanding of tea chemistry suggests that the antioxidants in the withered leaf (such as vitamin C and catechins) protect the already partially oxidised materials in the CTC dhool (i.e. the fresh catechins are preferentially oxidised to theaflavins and thearubigins, whilst those formed already are effectively stabilised. Example 2 illustrates the advantage of "co-rolling" CTC dhool and withered leaf, with the generation of greater than expected levels of theaflavins (one of the key components of black tea liquors).

An additional benefit from the process of the present invention is that smaller grades of tea tend to be generated. Those grades have been assessed by professional tea tasters and judged to deliver a surprising combination of colour and quality, both being very high. In conventional black tea manufacture such colour only tends to be found in small particles made using the CTC method, usually in combination with a long fermentation time and/or fermentation at high temperature. However under those conditions the tea tends to be of low quality, i.e. often dull and lacking flavour).

As an optional step to manipulate final grade profile the mixture can be sifted or sieved prior to drying, and any material judged to be larger then required can be either rolled again or cut in any fashion to reduce its size.

As a final step, the fermented mixture is fired and dried to yield a black leaf tea that resembles orthodox processed leaf tea but infuses in freshly boiled water at a rate in excess of that of the equivalent mass of the same tea that has undergone orthodox processing. Indeed the tea preferably infuses at a rate that is comparable to that of the equivalent mass of the same tea that has undergone CTC processing.

The firing involves heating and drying the tea to destroy the fermenting enzymes and thereby arrest fermentation. It results in a reduction of moisture content to below 5%, and also leads to further chemical/biochemical oxidation and changes in tea aroma. This generally involves exposing the tea to a blast of hot, dry air in a dryer, for example a fluid bed dryer.

The black leaf tea that is manufactured by the process of the present invention can be blended with traditionally processed black tea or tea granules in order to meet predetermined liquor characteristics.

The process of the invention will now be described with reference to the following illustrative examples.

EXAMPLE 1

Comparison of Black Tea Processes

Black leaf tea was manufactured according by the process of the invention (Process A; FIG. 1). Certain characteristics of infusions made from that tea were judged by a panel of experienced tea tasters (using the ISO methods for tea tasting, where each attribute is scored on a scale of 0.6 to 9.4, with differences of 0.2 being judged as significant) against the characteristics of infusions made from black leaf teas that were manufactured by the same process without any addition of CTC fermented dhool (Process B) and the same process with tea dust added rather than CTC fermented dhool (Process C).

In Process A the first supply of leaf was withered to a moisture content of 72%, macerated by passing through three CTC machines and fermented for 140 minutes at 22° C. This was mixed with a second supply of withered leaf (68% moisture content), in a ratio of 35% CTC dhool:65% withered leaf (dry weight basis). The mixture was passed through a 15" rotorvane, and then fermented for 140 minutes at 22° C., before drying in a conventional fluid bed dryer.

Process B was the same as A but with no addition of CTC dhool (i.e. 100% withered leaf passed through the rotorvane).

Process C was the same as A but with 35% wetted primary grade CTC dust (i.e. good quality material that had been dried and sorted as in conventional tea manufacture) added in place of the CTC fermented dhool.

The results are given in Table 1 below. For A, B and C BP1 size material was used (i.e. broken leaf), compared to a fannings/dust blend for the target CTC tea.

TABLE 1

Comparison of black leaf teas produced the process of the invention and variations thereof

|  | Colour | Quality | Brightness | Thickness |
| --- | --- | --- | --- | --- |
| Target CTC blend | 4.4 | 5.0 | 5.0 | 4.4 |
| Process A | 4.2 | 5.0 | 5.0 | 4.4 |
| Process B | 2.6 | 5.6 | 5.0 | 4.2 |
| Process C | 3.2 | 5.0 | 5.4 | 4.6 |

These results show that mixing CTC fermented dhool with withered green tea leaves prior to rolling provides a significant enhancement in the colour of the tea, but not at the expense of the desired overall flavour/quality.

These results show that mixing CTC fermented dhool with withered green tea leaves prior to rolling provides a significant enhancement in the colour of the tea, but not at the expense of the desired overall flavour/quality.

Colour scores virtually match the CTC tea (4.2 vs. 4.4), compared to 3.2 where dust was used and only 2.6 for rotorvane only tea. The quality score, which includes an assessment of flavour, also matches the target blend (the rotorvane only tea scores higher here, as expected due to the naturally higher flavours seen in rolled, orthodox-type teas). In addition adding dhool rather than wetted dust gives a significant advantage in terms of colour delivery (due to the biochemical interactions discussed earlier).

Adding dust gives a product of good quality since, in contrast to the practice of "reconditioning" referred to earlier, high quality dust was used as the additive.

Figure 2:
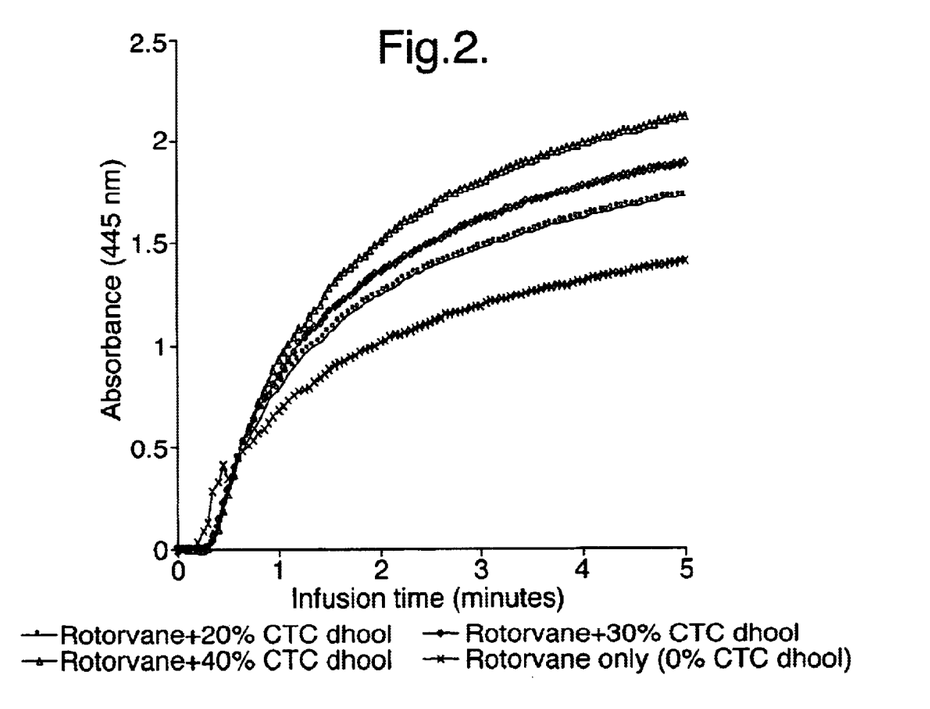
FIG. 2 shows infusion curves as measured by colour delivery of a range of teas manufactured according to the process of the present invention.

FIG. 2 shows infusion curves as measured by colour delivery (2 g tea infused in 200 ml water at 90° C., infusion monitored at 445 nm) of a range of teas manufactured according to the process of the present invention (as in A above), with levels of CTC dhool addition ranging from 0 to 40%. The benefit of adding CTC dhool can clearly be seen, with a step-change in colour delivery, which increases with increasing percentage CTC dhool addition. Significantly all of the samples (0 to 40% CTC dhool addition) had the same leaf appearance, that of a leafy orthodox tea rather than a blend of leaf and granular CTC teas.

EXAMPLE 2

Comparison of Black Tea Processes

Black leaf tea was manufactured according to the process of the invention (Process A), by the same process minus the addition of fermented CTC dhool (Process B), and by a standard CTC method (Process C). Starting green leaf was from the same batch for all three manufacturing runs. Levels of theaflavins (TF) were analysed throughout fermentation. Theaflavins are key components of black tea liquors, being generated during oxidative reactions in fermentation, contributing to both liquor appearance (colour and brightness) and taste.

In Process A the first supply of leaf was withered to a moisture content of 72%, macerated by passing through three CTC machines and fermented for 140 minutes at 22° C. The fermented macerated leaves were mixed with a second supply of withered leaf (68% moisture content), in a ratio of 35% CTC dhool:65% withered leaf (dry weight basis). The mixture was passed through a 15" rotorvane, and then fermented for 140 minutes at 22° C., before drying in a conventional fluid bed dryer.

Process B was the same but with no addition of CTC dhool (i.e. 100% withered leaf passed through the rotorvane).

In Process C the leaves were withered to a moisture content of 72%, macerated by passing through three CTC machines and fermented for 140 minutes at 22° C.

Figure 3:
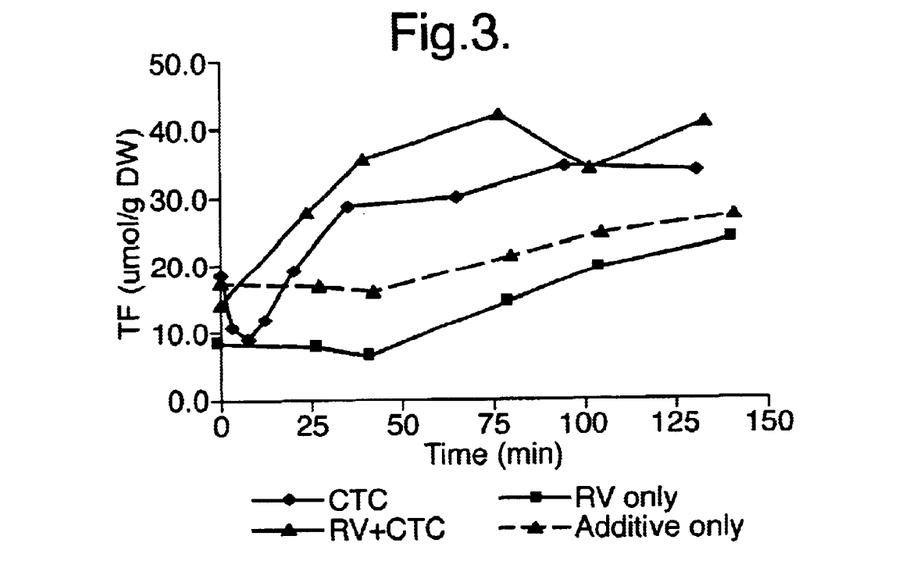
FIG. 3 shows levels of total theaflavins through fermentation.

The results are shown in FIG. 3.

FIG. 3 shows levels of total theaflavins or TFs (i.e. theaflavin, theaflavin 3 monogallate, theaflavin 3'monogallate and theaflavin digallate) through fermentation. Theaflavins accumulated at a faster rate and to a higher end level when leaf was manufactured according to Processes A and C than when manufactured by Process B. Given that theaflavin species contribute significantly to liquor colour, this data supports tasting results from Example 1 showing that addition of fermented CTC dhool before rotorvane maceration leads to enhancement of infusion colour.

Addition of fermented CTC dhool to process B would be expected to lead to an increase of theaflavin levels, since fermented CTC dhool contains relatively high levels of theaflavins compared to fermenting dhool from Process B. However, the inventors were surprised to find that the addition of CTC dhool results in an increase in theaflavins in the dhool of Process A, which is larger than would be predicted by a purely additive relationship. This principle is illustrated in FIG. 1 by comparing the rate and extent of theaflavin accumulation in Process A with the dashed line representing theoretical theaflavin levels calculated according to the equation:

[TF]=(35% process C [TF] at t=140)+(65% process B [TF])

The inventors speculate that this unexpected increase in theaflavins may be due to either addition of extra oxidative enzymes in the CTC dhool and/or a physical disruption of rotorvaned leaf by the CTC particles, leading to an enhanced rate of fermentation Theaflavin Analysis Samples of approximately 10 g fresh weight dhool were taken at various points through fermentation and quick frozen on dry ice before being freeze-dried. Freeze-dried material was ground to a fine powder in a pestle and mortar. Approximately 0.2 g ground material was extracted with 5 ml 70% (v/v) methanol for 10 minutes at 70° C., cooled and centrifuged at 2,500 rpm for 10 minutes. The supernatant was decanted and the pellet re-extracted. The two supernatant fractions were then combined, made up to 10 ml with 70% methanol before the addition of 250 ppm EDTA and 250 ppm ascorbic acid to stabilise the sample.

High Performance Liquid Chromatography (HPLC) was performed on a DIONEX™ system with a AS3500 autosampler and GP40 gradient pump. A photodiode array detector (DIONEX PD40) was used to record spectra of compounds eluting from the column on-line. Peak purity, identification and integration were carried out on DIONEX EZChrom™ software (version 2). Column and run details are given in Table 2 below:

TABLE 2

| Column and run details | | | | |
|---|---|---|---|---|
| Step | Time | % A | % B | |
| 1 | 20 min | 15–25 | 85–75 | linear gradient |
| 2 | 10 min | 15 | 85 | wash/equilibrate |

| | |
|---|---|
| Solvent A: | 2% acetic acid in acetonitrile |
| Solvent B: | 2% acetic acid in de-ionised water |
| Flow rate: | 2 ml/min |
| Column Temperature: | 30° C. |
| Detection: | 274 nm |
| Injection volume: | 40 µl |
| Column details: | HYPERSIL ™ 3 µm C18 |
| | 100 × 4.6 mm - PHENOMENEX ™ |

Catechin and Theaflavin Analysis

Catechin and theaflavin analysis was also performed on various fractions of the made teas from these trials. The results are shown in Table 3 below and FIGS. 4 and 5.

TABLE 3

| Analysis of catechins and theaflavins | | |
|---|---|---|
| Method | Catechins µg/g DW | Theaflavins µg/g DW |
| CTC PD | 50.00 | 36.30 |
| CTC PF1 | 50.04 | 38.22 |
| CTC BP1 | 60.01 | 26.26 |
| RV PD | 58.39 | 38.77 |
| RV PF1 | 113.62 | 29.99 |
| PV BP1 | 120.66 | 21.26 |
| RV + CTC PD | 38.08 | 42.45 |
| RV + CTC PF1 | 64.91 | 38.63 |
| RV + CTC BP1 | 93.94 | 31.93 |

Figure 4:
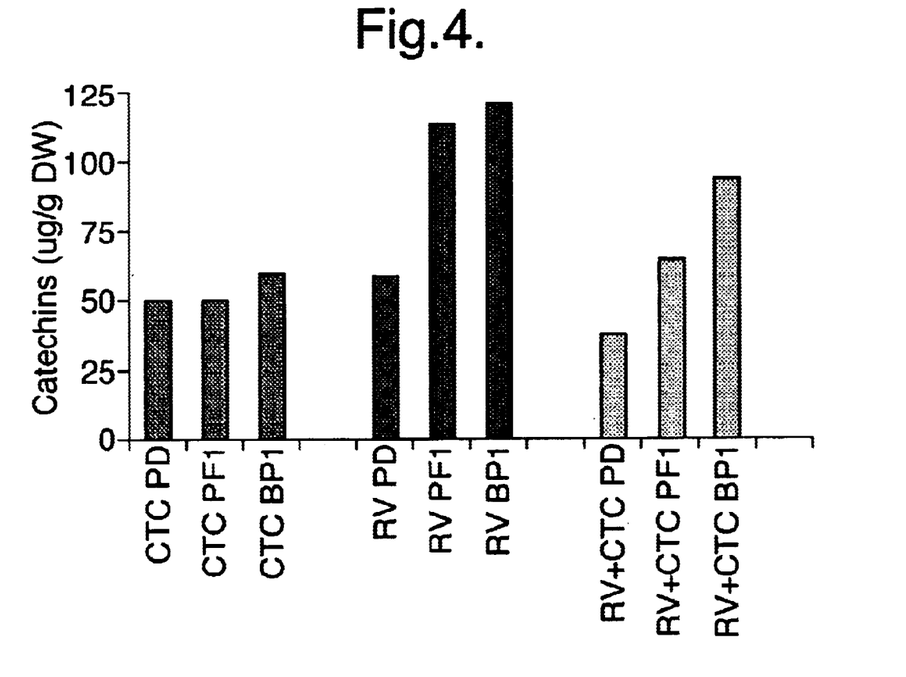
FIGS. 4 and 5 show catechin and theaflavin analysis performed on various fractions of the teas produced by the present invention.
Figure 5:
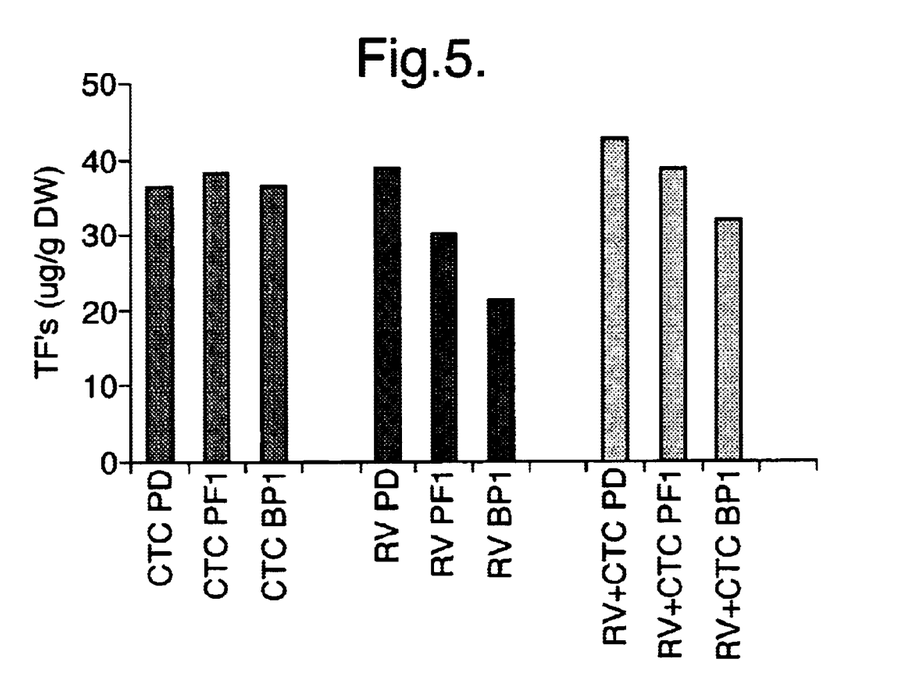

From this table and the FIGS. 4 and 5 it is clear that larger size grades from the Rotorvane (RV) only processed samples have higher levels of catechins and less theaflavins than the smaller grades. That suggests incomplete fermentation, consistent with the lower colour scores given by the tea taster. The three size grades of CTC processed teas have similar levels of catechins and theaflavins, as expected as the larger size grades tend to be aggregates of smaller particles. The three grades from the process of the invention (Process A i.e. CTC+RV) have theaflavin levels much closer to those of the CTC process, again consistent with the enhanced liquor colours of these teas.

EXAMPLE 3

Analysis of Glycoside Derived Volatiles

The experiments in Example 2 were repeated, and macerated leaf samples were taken for volatile (aroma) analysis (40.0 g of leaf was blended in 250 ml saturated $CaCl_2$ solution in order to arrest any enzyme activity during thawing. Lickens Nickersen extraction was then carried out into 25 ml of a 50:50 n-pentane/diethyl ether mixture. 5 ml of the cyclohexanal internal standard (100 ppm) was added to the leaf/water mixture prior to extraction. Each sample was extracted in duplicate for 3 hours. The solvent extract was concentrated to a final volume of 1.0 ml of which 3 $\mu l$ was injected onto the gas chromatographic column). The results are shown in FIG. 6.

Figure 6:
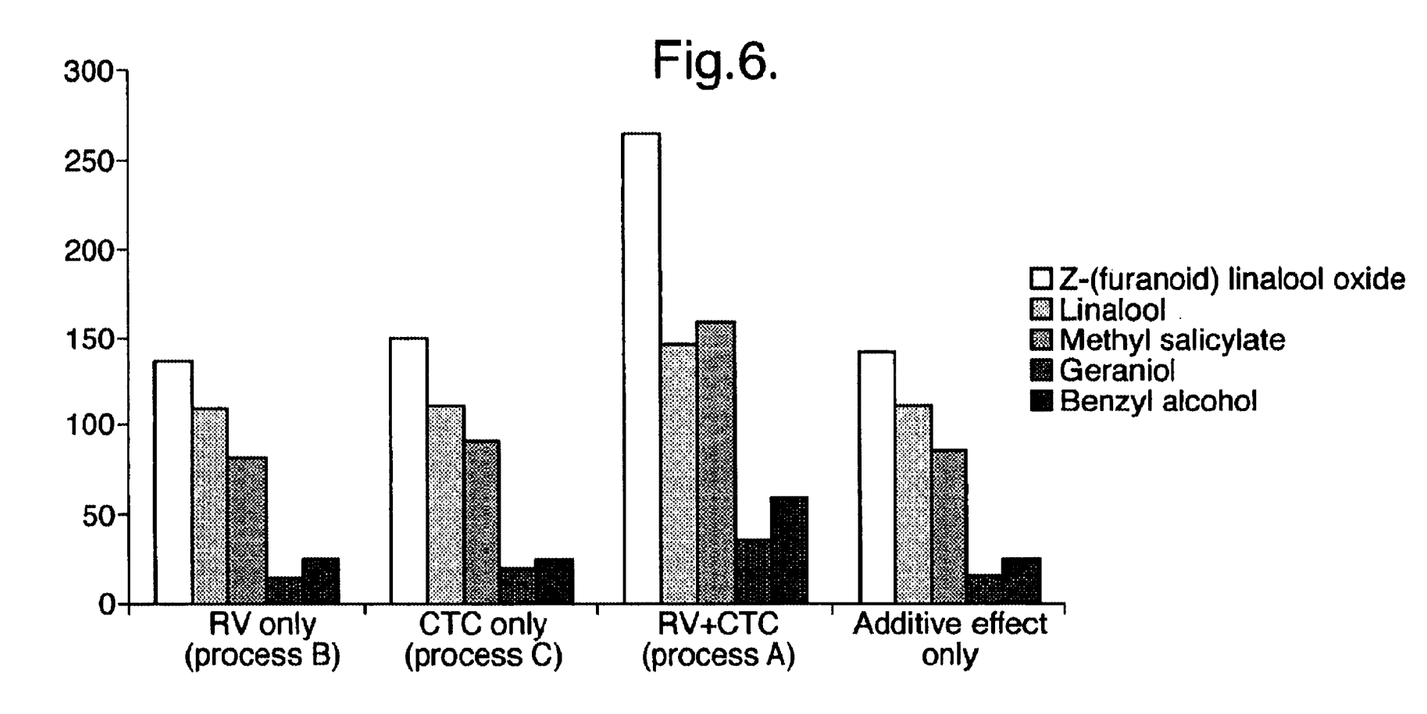
FIG. 6 shows the levels of glycoside derived volatiles in the leaf taken from the process of the present invention, by the same process minus the addition of fermented CTC dhool, and from a standard GTC process.

FIG. 6 shows the levels of glycoside derived volatiles in the leaf taken from the process of the invention (Process A), by the same process minus the addition of fermented CTC dhool (Process B) and from a standard CTC process (Process C). In addition the amount of volatiles expected from the combination of the RV only and CTC only is also shown (i.e. the amount expected in the current process of the invention if there were no interaction between the two leaf sources).

It can clearly be seen that the levels of glycoside-derived volatiles were higher in the process of the invention, than either RV only or CTC only, and therefore of the theoretical combination. This suggested an interaction between the two leaf streams in the maceration/mixing process, possibly glycosidases from the small CTC particles acting on substrates in the withered leaf.

Following fermentation and drying the levels of volatiles in the product of the current process were found to be similar to those in the CTC tea, and higher than the RV only. It was also found that much of the volatiles are lost in the latter part of the process (drying; up to 80% of the total), and it appeared that orthodox leaf (perhaps due to its more open structure) lost more volatiles than the agglomerated, granular CTC particles. It therefore seemed beneficial that the leaf of the current process had higher volatiles pre-drying, such that post-drying the levels were similar to the CTC target (as shown in the quality scores of the tea tasters, and revealed in sensory analysis).

EXAMPLE 4

Effect of Tannase Treatment on Gallic Acid Content

Green CTC dhool was treated with either tannase (80 mg/kg dhool), or water only (control) and fermented for 120 min. Tannase treatment facilitates the hydrolysis of gallate esters to release free gallic acid. As a consequence the resulting fermented dhool contained either 146 mg gallic acid/g DW (tannase treated) or 21 mg gallic acid/g DW (control).

This fermented dhool was used in the process of the invention, added to fresh (withered) green leaf at a ratio of 35% dhool:65% leaf before undergoing subsequent processing in the RV. Dried tea was size graded and the gallic acid content analysed using HPLC.

Tannase treatment of CTC dhool resulted in an increase in gallic acid content. When this CTC dhool was used as the addback, the resulting made tea also contained increased amounts of gallic acid.

Figure 7:
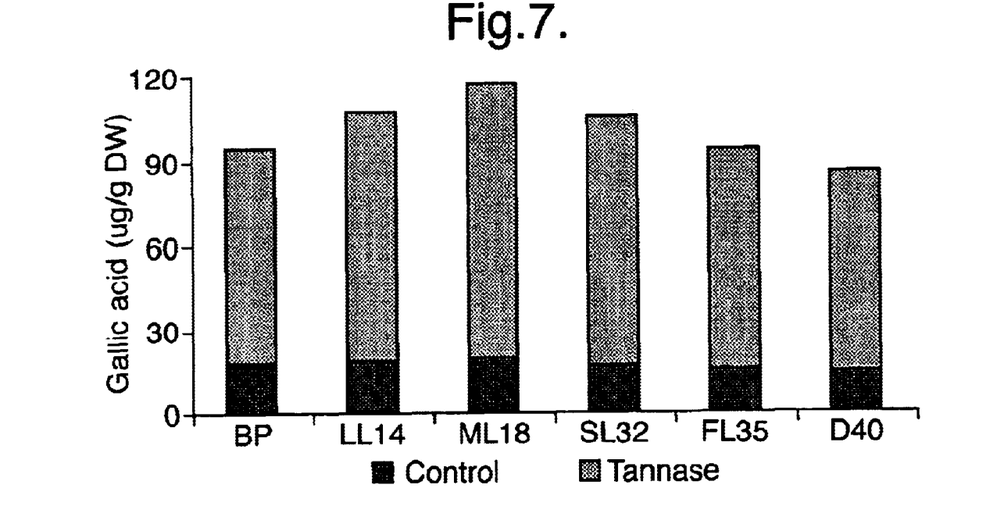
FIG. 7 shows the respective gallic acid contents of various grades of tea made by the process of the present invention.

The respective gallic acid contents of various grades of tea made by the process of the present invention are given in FIG. 7.

The observation that enhanced levels of gallic acid are present in all tea grades provides additional evidence for an interaction between CTC and RV leaf since, if there were no such interaction, it would be expected that increased gallic acid would only be present in the smaller CTC size grades. Interactions between CTC dhool and RV leaf may occur via a physical association of CTC particles with RV particles and/or the transfer of soluble gallic acid from CTC particles to RV dhool during the mixing (rotorvane) step.

EXAMPLE 5

Effect of Fermentation Time

The experiments in Example 2 were repeated, and in addition a second CTC trial was carried out, with a fermentation time of 280 min (equivalent to the "standard" 150 minutes of the CTC component of the RV+CTC process, and the subsequent fermentation of the leaf/CTC dhool mixture post-maceration). Sensory analysis was performed by a trained panel. The results revealed that significant changes were found between CTC tea fermented for 150 minutes and 280 minutes in terms of liquor appearance (increases in redness, darkness and opacity) and flavour (increases in non-desirable attributes such as fruity and jammy). These increases in colour and flavour attributes were not seen in the RV+CTC tea, again suggesting that interactions between the two leaf types ("fresh" withered leaf and CTC dhool) protect the key quality components generated in the CTC dhool after the first 150 minute fermentation.

EXAMPLE 6

Generation of Small Grades

Tea made according to the process of the present invention was sorted and graded. The smaller grades, i.e. SL (Small Leaf or small fanning), FL (Fine Leaf or large dust) and D (dust) were assessed by professional tea tasters and scored in accordance with a system whereby Q denotes quality, with 0.6 being plain and 9.4 being flavoury; C denotes colour, with 0.6 being yellow and 9.4 being red; B denotes brightness, with 0.6 being dull and 9.4 being bright; and T denotes thickness with 0.6 being thin and 9.4 being thick. The results as given in Table 4 below:

TABLE 4

Sensory analysis of smaller tea grades

| | Mean taster scores | | | |
|---|---|---|---|---|
| Grade | Q | C | B | T |
| SL | 4.7 | 6.8 | 5.1 | 4.8 |
| FL | 4.5 | 7.0 | 5.1 | 5.4 |
| D | 4.3 | 6.8 | 4.7 | 5.8 |

These small grades were judged to deliver a surprising combination of colour and quality, both being very high. In conventional black tea manufacture such colour only tends to be found in small particles made using the CTC method, usually in combination with a long fermentation time and/or fermentation at high temperature. However under those conditions the tea tends to be of low quality, i.e. often dull and lacking flavour).

For the SL grade, teas from Malawi would be the nearest conventional equivalent. Those with a colour (C) score of 6.8 would typically have a quality (Q) score of 3.2 to 4.0.

Nearest conventional equivalent to the FL and D grades would be from Argentina. A tea with a colour (C) score of 7.0 would typically have a quality (Q) score of 2.8 to 3.8.

Conventional teas typically have a Q score of 1.0 to 1.4 units lower than teas made according to the process of the present invention with the same C score.

What is claimed is:

1. A process for manufacturing black tea comprising the steps of:

withering a first supply of freshly plucked tea leaves, macerating the withered leaves, allowing the macerated withered leaves to ferment to produce macerated dhool having a high moisture content;

withering a second supply of freshly plucked tea leaves;

mixing the macerated dhool obtained from said first supply of leaves with the withered leaves obtained from said second supply of leaves, rolling the mixture, allowing the rolled mixture to ferment;

and drying the fermented mixture to yield black leaf tea.

2. A process according to claim 1 wherein the first supply of freshly plucked tea leaves is passed through a CTC machine to macerate it.

3. A process according to claim 1 wherein the first supply of freshly plucked tea leaves is passed through a rotorvane machine and a CTC machine to macerate it.

4. A process according to claim 1 wherein the macerated dhool is treated with tannase acid to generate colour and enhance flavour.

5. A process according to claim 1 wherein the macerated dhool is treated with tannase and hydrogen peroxide to generate colour and enhance flavour.

6. A process according to claim 1 wherein the macerated dhool comprises between 10 and 50% of the mixture on a dry weight basis.

7. A process according to claim 1 wherein the mixture is passed through a rotorvane machine to roll it.

8. A process according to claim 1 wherein the macerated dhool has a moisture content of 62 to 74%.

* * * * *